(12) United States Patent
Deane et al.

(10) Patent No.: US 11,969,228 B2
(45) Date of Patent: Apr. 30, 2024

(54) CONTROLLING A SURGICAL INSTRUMENT

(71) Applicant: CMR SURGICAL LIMITED, Cambridge (GB)

(72) Inventors: Gordon Thomas Deane, Cambridge (GB); Graham John Veitch, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 808 days.

(21) Appl. No.: 17/075,773

(22) Filed: Oct. 21, 2020

(65) Prior Publication Data
US 2021/0113287 A1 Apr. 22, 2021

(30) Foreign Application Priority Data
Oct. 22, 2019 (GB) .................................... 1915270

(51) Int. Cl.
*A61B 34/00* (2016.01)
*A61B 17/062* (2006.01)
(Continued)

(52) U.S. Cl.
CPC ............ *A61B 34/74* (2016.02); *A61B 17/062* (2013.01); *A61B 17/282* (2013.01);
(Continued)

(58) Field of Classification Search
CPC ..... A61B 34/74; A61B 17/062; A61B 17/282; A61B 17/3201; A61B 34/71; A61B 34/37;
(Continued)

(56) References Cited

U.S. PATENT DOCUMENTS

| 5,954,731 A | * | 9/1999 | Yoon | .................... A61B 17/062 |
| | | | | 606/147 |
| 2003/0060927 A1 | | 3/2003 | Gerbi et al. | |

(Continued)

FOREIGN PATENT DOCUMENTS

| EP | 2617530 A1 | 7/2013 |
| GB | 2560384 A  | 9/2018 |

(Continued)

OTHER PUBLICATIONS

United Kingdom Search Report from corresponding United Kingdom Application No. GB1915270.1 dated Mar. 24, 2020.
(Continued)

*Primary Examiner* — Jason Holloway
(74) *Attorney, Agent, or Firm* — Lando & Anastasi, LLP

(57) ABSTRACT

A control system configured to control manipulation of a surgical instrument in response to manipulation of a remote surgeon input device. The surgical instrument comprises an end effector having opposable first and second end effector elements connected to a shaft by an articulated coupling. The control system receives a command from the surgeon input device to both (i) change the orientation of the end effector, and (ii) open the first and second end effector elements relative to each other. In response to the command to change the orientation of the end effector, the control system determines an angle θ between the longitudinal axis of the articulated coupling and the end effector. In response to the command to open the first and second end effector elements, the control system determines an opening angle φ between the first and second end effector elements. The control system compares θ to a maximum angle $θ_{max}$ between the longitudinal axis of the articulated coupling and the end effector, and if $θ > θ_{max}$, drives the first and second end effector elements to rotate such that (i) the angle between the longitudinal axis of the articulated coupling and (Continued)

the end effector is $\theta_{max}$, and (ii) the opening angle between the first and second end effector elements is $\phi$.

19 Claims, 6 Drawing Sheets

(51) Int. Cl.
  *A61B 17/28* (2006.01)
  *A61B 17/3201* (2006.01)
  *G16H 20/40* (2018.01)
  *G16H 40/67* (2018.01)
  *A61B 34/37* (2016.01)
  *A61B 90/50* (2016.01)

(52) U.S. Cl.
  CPC .......... *A61B 17/3201* (2013.01); *A61B 34/71* (2016.02); *G16H 20/40* (2018.01); *G16H 40/67* (2018.01); *A61B 34/37* (2016.02); *A61B 90/50* (2016.02)

(58) Field of Classification Search
  CPC .......... A61B 90/50; A61B 34/30; A61B 34/35; A61B 2034/305; G16H 20/40; G16H 40/67
  See application file for complete search history.

(56) References Cited

U.S. PATENT DOCUMENTS

| 2009/0088774 | A1  | 4/2009  | Swarup et al. |
| 2015/0051629 | A1* | 2/2015  | Abri .................... A61B 17/29 |
|              |     |         | 606/174 |
| 2018/0325611 | A1  | 11/2018 | Robinson et al. |
| 2021/0145532 | A1* | 5/2021  | Tucker .................... A61B 34/74 |

FOREIGN PATENT DOCUMENTS

| WO | 2017083201 A1 | 5/2017 |
| WO | 2017151996 A1 | 9/2017 |
| WO | 2018044306 A1 | 3/2018 |

OTHER PUBLICATIONS

Japanese Notification of Reasons for Refusal from corresponding Japanese Application No. 2022-523698 dated May 16, 2023.
Notification of Transmittal of the International Search Report and the Written Opinion of the International Searching Authority from corresponding PCT/GB/2020/052649 dated Jan. 20, 2021.

* cited by examiner ized by multiple flexible joints 108 along its length, which are used to locate the surgical instrument in a desired location relative to the patient. The surgical instrument is attached to the distal end of the robot arm. The surgical instrument penetrates the body of the patient at a port so as to access the surgical site. At its distal end, the instrument comprises an end effector 110 for engaging in a surgical procedure. In FIG. 1, the illustrated end effector is a pair of jaws. A surgeon controls the surgical robot 100 via a remote surgeon console 112. The surgeon console comprises one or more surgeon input devices 114. These may take the form of a hand controller or foot pedal. The surgeon console also comprises a display 116.

A control system 118 connects the surgeon console 112 to the surgical robot 100. The control system receives inputs from the surgeon input device(s) and converts these to control signals to move the joints of the robot arm 104 and end effector 110. The control system sends these control signals to the robot, where the corresponding joints are driven accordingly.

It is known for the jaws of an end effector to be individually driven by cables. These cables may be utilised to drive opening and closing of the jaws so as to grip and release an object between them. The same cables may also be used to drive a yawing motion of the jaws so as to cause the jaws to rotate in the same direction with the opening angle of the jaws remaining constant. Since the same cables are used to drive both the opening/closing and yawing motion of the jaws, these operations are not independent. As a result of this, the whole range of opening/closing motion cannot be accessed over the whole range of yawing motion, and vice versa.

Thus, there is a need for a control system which better mediates the interdependence of the opening/closing and yawing motion of an end effector.

CONTROLLING A SURGICAL INSTRUMENT

CROSS-REFERENCE TO RELATED APPLICATION

This application claims the benefit under 35 U.S.C. § 119 of United Kingdom Patent Application No. 1915270.1 filed on Oct. 22, 2019 which is hereby incorporated herein by reference in its entirety for all purposes.

BACKGROUND

It is known to use robots for assisting and performing surgery. FIG. 1 illustrates a typical surgical robotic system. A surgical robot 100 consists of a base 102, an arm 104 and an instrument 106. The base supports the robot, and may itself be attached rigidly to, for example, the operating theatre floor, the operating theatre ceiling or a cart. The arm extends between the base and the instrument. The arm is articu-

SUMMARY OF THE INVENTION

According to an aspect of the invention, there is provided a control system for controlling manipulation of a surgical instrument in response to manipulation of a remote surgeon input device, the surgical instrument comprising an end effector having opposable first and second end effector elements connected to a shaft by an articulated coupling, the control system configured to: receive a command from the surgeon input device to both (i) change the orientation of the end effector, and (ii) open the first and second end effector elements relative to each other; in response to the command to change the orientation of the end effector, determine an angle $\theta$ between the longitudinal axis of the articulated coupling and the end effector; in response to the command to open the first and second end effector elements, determine an opening angle $\phi$ between the first and second end effector elements; compare $\theta$ to a maximum angle $\theta_{max}$ between the longitudinal axis of the articulated coupling and the end effector; and if $\theta > \theta_{max}$, drive the first and second end effector elements to rotate such that (i) the angle between the longitudinal axis of the articulated coupling and the end effector is $\theta_{max}$, and (ii) the opening angle between the first and second end effector elements is $\phi$.

The control system may be configured to, if $\theta \leq \theta_{max}$, drive the first and second end effector elements to rotate such that (i) the angle between the longitudinal axis of the articulated coupling and the end effector is $\theta$, and (ii) the opening angle between the first and second end effector elements is $\phi$.

The angle $\theta$ may be between the longitudinal axis of the articulated coupling and an axis which bisects the end effector elements. $\theta_{max}$ may be a function of $\phi$ and $\alpha_{max}$, where $\alpha_{max}$ is the maximum rotation from the longitudinal axis of the articulated coupling of the end effector element in the commanded direction of rotation.

Optionally, $\theta_{max} = \alpha_{max} - \phi/2$.

The control system may be configured to determine the opening angle $\phi$ between the first and second end effector elements by: in response to the command to open the first and second end effector elements, determine an opening angle $\psi$; compare $\psi$ to a maximum angle $\phi_{max}$ between the first and second end effector elements; and if $\psi > \phi_{max}$, drive the first and second end effector elements to rotate such that the opening angle between the first and second end effector elements $\phi = \phi_{max}$.

The control system may be configured to, if $\psi \leq \phi_{max}$, drive the first and second end effector elements to rotate such that the opening angle between the first and second end effector elements $\phi = \psi$.

The command from the surgeon input device to change the orientation of the end effector may comprise a rotation of at least a portion of the surgeon input device in its workspace.

The surgeon input device may comprise a body and a trigger, and the command from the surgeon input device to open the first and second end effector elements relative to each other may comprise a movement of the trigger relative to the body.

The command from the surgeon input device to open the first and second end effector elements relative to each other may comprise a rotation of the trigger away from the body.

The angle between the trigger and the body at the end of the rotation may be proportional to $\phi$.

The command from the surgeon input device to open the first and second end effector elements relative to each other may comprise a linear translation of the trigger relative to the body.

The articulated coupling may comprise a first joint driveable by a first pair of driving elements, and a second joint driveable by a second pair of driving elements. The control system may be configured to drive the first and second end effector elements to rotate by: commanding a first force to be applied to the first pair of driving elements so as to cause the first end effector element to rotate about the first joint; and commanding a second force to be applied to the second pair of driving elements so as to cause the second end effector element to rotate about the second joint.

The articulated coupling may further comprise a third joint driveable by a third pair of driving elements. The control system may be configured to: in response to the command to change the orientation of the end effector, determine an angle Ω between the longitudinal axis of the shaft and the articulated coupling; and drive the end effector to rotate about the third joint by Ω.

The control system may be configured to drive the end effector to rotate about the third joint by commanding a third force to be applied to the third pair of driving elements so as to cause the end effector to rotate about the third joint.

The control system may be configured to: following driving the first and second end effector elements to rotate such that the angle between the longitudinal axis of the articulated coupling and the end effector is $\theta_{max}$, receive a further command from the surgeon input device to increase the opening angle between the first and second end effector elements relative to each other; in response to the further command: determine an opening angle $\phi'$ between the first and second end effector elements; determine an angle $\theta_{max}'$ between the longitudinal axis of the articulated coupling and the end effector, where $\theta_{max}'$ is a function of $\phi'$; and drive the first and second end effector elements to rotate such that (i) the angle between the longitudinal axis of the articulated coupling and the end effector is $\theta_{max}'$, and (ii) the opening angle between the first and second end effector elements is $\phi'$.

Optionally, $\theta_{max}' = \alpha_{max} - \phi'/2$, where $\alpha_{max}$ is the maximum rotation from the longitudinal axis of the articulated coupling of the end effector element in the commanded direction of rotation.

Each of the first and second pairs of driving elements may comprise cables.

The first force, second force and/or third force may be tension forces.

The opposable first and second end effector elements may be one of: a pair of jaws, a pair of scissors, and a needle driver.

BRIEF DESCRIPTION OF THE FIGURES

The present invention will now be described by way of example with reference to the accompanying drawings. In the drawings.

DETAILED DESCRIPTION

Figure 1:
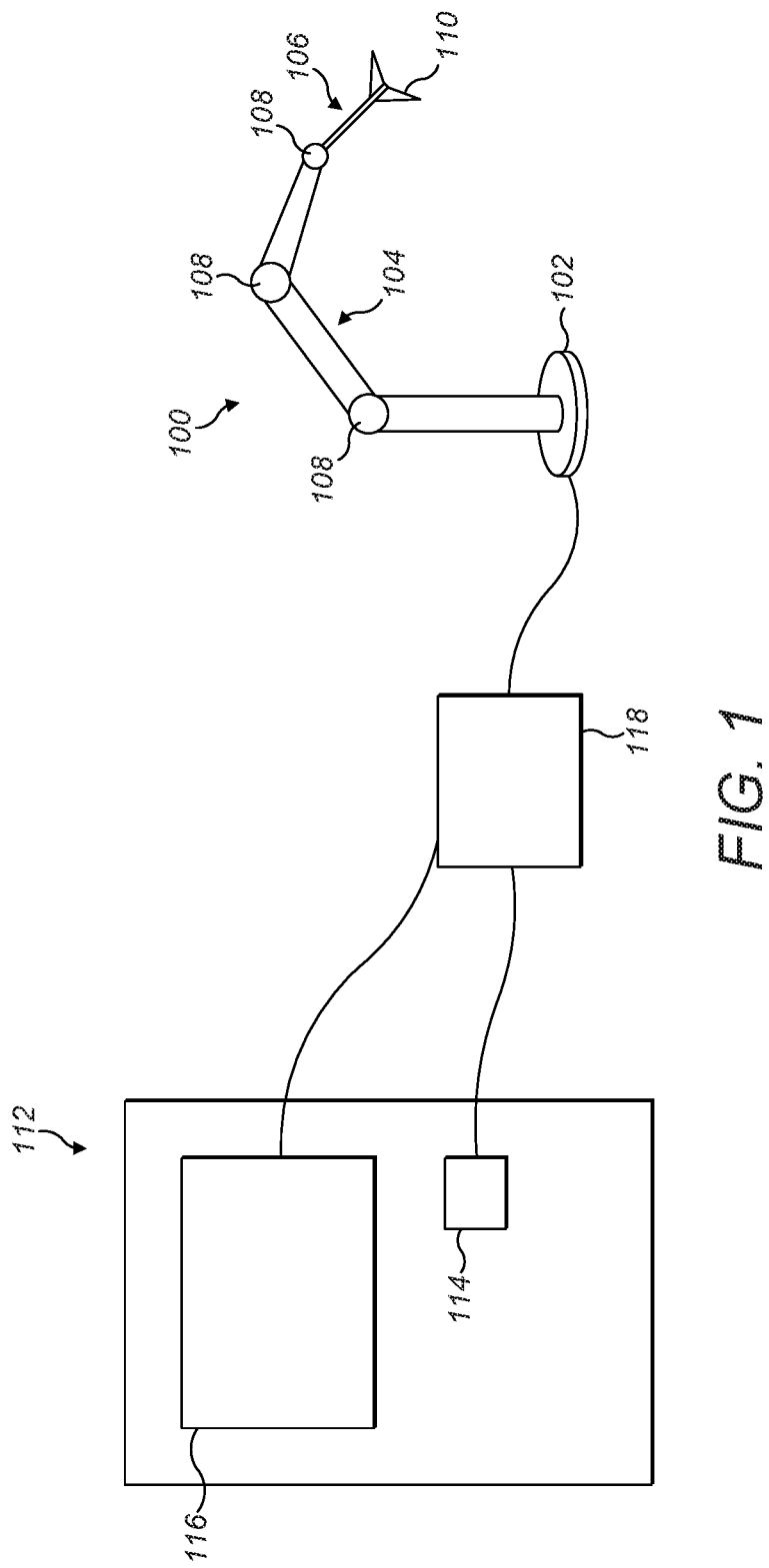
FIG. 1 illustrates a surgical robot system for performing a surgical procedure.

The following describes controlling a surgical robotic instrument from a remote surgeon console. The instrument and console form part of a surgical robotic system of the type illustrated in FIG. 1.

The surgical instrument is supported by a robot arm. The robot arm is itself supported by a base. During surgery, the base is secured to part of the operating theatre, for example the floor, ceiling, cart or patient bed. The robot arm remains at all times external to the patient. The robot arm comprises a series of arm links interspersed with joints. These joints may be revolute joints. The end of the robot arm distal to the base can be articulated relative to the base by movement of one or more of the joints. The surgical instrument attaches to a drive assembly at the distal end of the robot arm. This attachment point is external to the patient.

The surgical instrument has an elongate profile, with a shaft spanning between its proximal end which attaches to the robot arm and its distal end which accesses the surgical site within the patient body. The proximal end of the surgical instrument and the instrument shaft may be rigid with respect to each other and rigid with respect to the distal end of the robot arm when attached to it. An incision is made into the patient body, through which a port is inserted. The surgical instrument may penetrate the patient body through the port to access the surgical site. Alternatively, the surgical instrument may penetrate the body through a natural orifice of the body to access the surgical site. At the proximal end of the instrument, the shaft is connected to an instrument interface. The instrument interface engages with the drive assembly at the distal end of the robot arm. Specifically, individual instrument interface elements of the instrument interface engage individual drive assembly interface elements of the drive assembly. The instrument interface is releasably engageable with the drive assembly. The instrument can be detached from the robot arm manually without requiring any tools. This enables the instrument to be detached from the drive assembly quickly and another instrument attached during an operation.

Figure 2A:
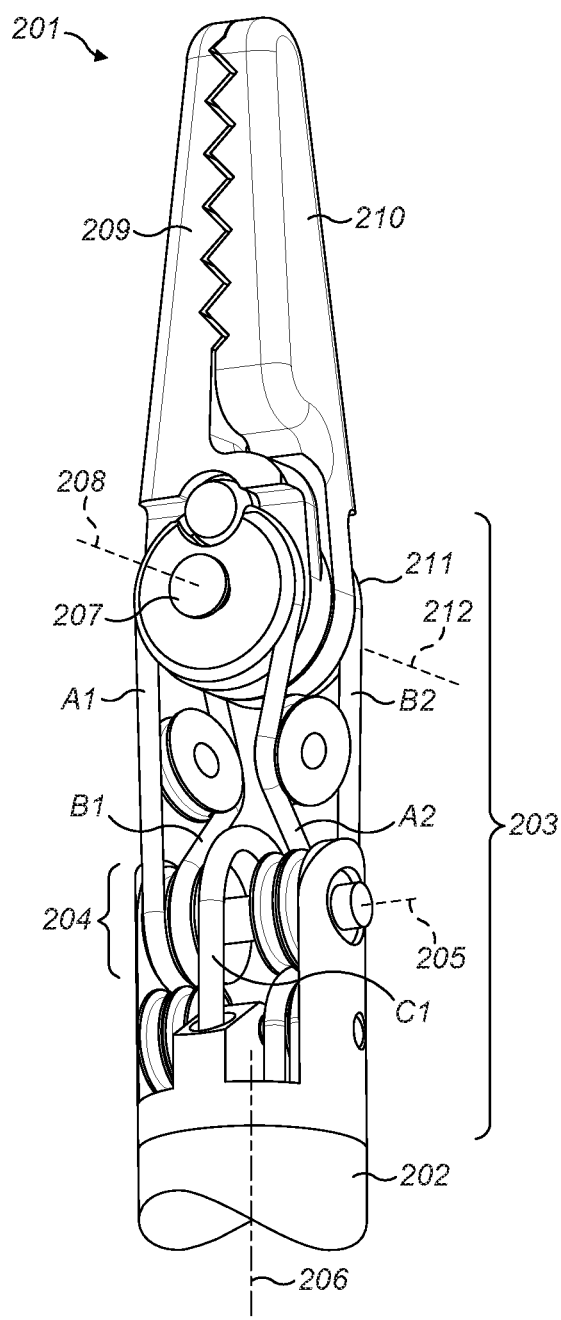
FIGS. 2a and 2b illustrates the distal end of an exemplary surgical instrument.
Figure 2B:
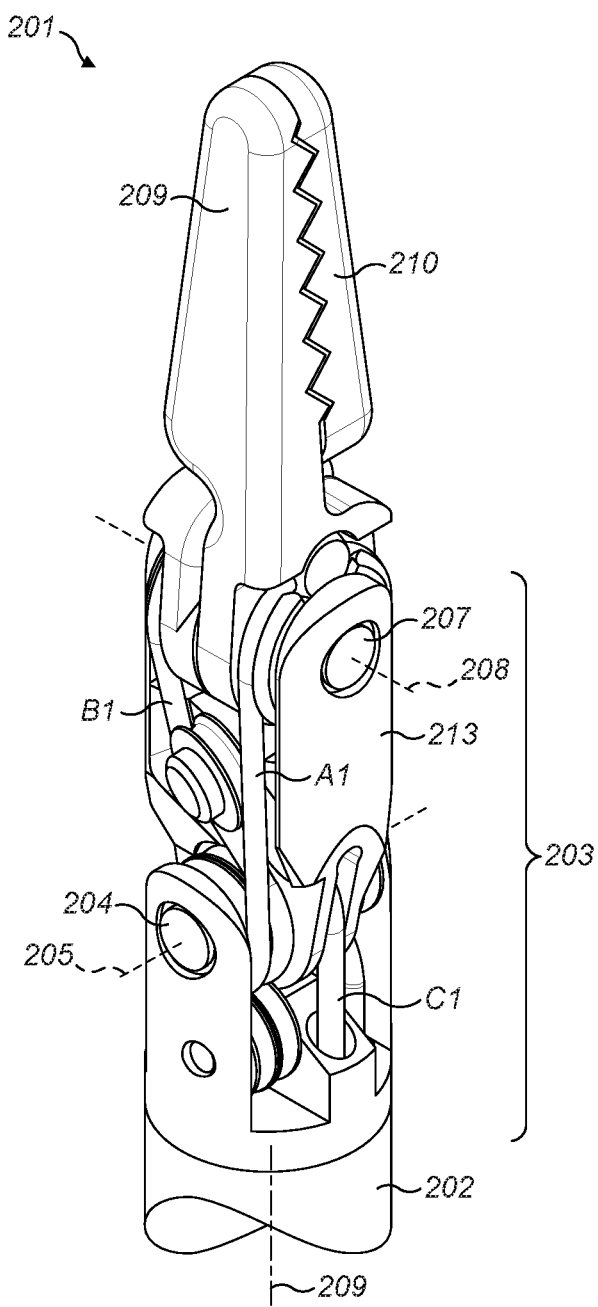

At the distal end of the surgical instrument, the shaft is connected to an end effector by an articulated coupling. The end effector engages in a surgical procedure at the surgical site. FIGS. 2a and 2b illustrate the distal end of an exemplary instrument which has a pair of jaws as the end effector 201. The shaft 202 is connected to the end effector 201 by articulated coupling 203. The articulated coupling 203 comprises several joints. These joints enable the pose of the end effector to be altered relative to the direction of the instrument shaft. Although not shown in FIGS. 2a and 2b, the end effector may also comprise joint(s). In the example of FIGS. 2a and 2b, the articulated coupling 203 comprises a pitch joint 204. The pitch joint 204 rotates about pitch axis 205, which is perpendicular to the longitudinal axis 206 of the shaft 202. The pitch joint 204 permits a supporting body 213 (described below) and hence the end effector 201 to rotate about the pitch axis 205 relative to the shaft. In the example of FIGS. 2a and 2b, the articulated coupling also comprises a first yaw joint 207 and a second yaw joint 211. First yaw joint 207 rotates about first yaw axis 208. Second yaw joint 211 rotates about second yaw axis 212. Both yaw axes 208 and 212 are perpendicular to pitch axis 205. Yaw axes 208 and 212 may be parallel. Yaw axes 208 and 212 may be collinear. The articulated coupling 203 comprises a supporting body 213. At one end, the supporting body 213 is connected to the shaft 202 by pitch joint 204. At its other end, the supporting body 213 is connected to the end effector 201 by the yaw joints 207 and 211. This supporting body is omitted from FIG. 2a for ease of illustration so as to enable the other structure of the articulated coupling to be more easily seen. The end effector 201 comprises two end effector elements 209, 210. The end effector elements shown are opposing jaws. However, the end effector elements may be any type of opposing end effector elements, further examples of which are discussed later. The first yaw joint 207 is fast with the first end effector element 209 and permits the first end effector element 209 to rotate about the first yaw axis 208 relative to the supporting body 213 and the pitch joint 204. The second yaw joint 211 is fast with the second end effector element 210 and permits the second end effector element 210 to rotate about the second yaw axis 212 relative to the supporting body 213 and the pitch joint 204.

The joints illustrated in FIGS. 2a and 2b are driven by pairs of driving elements. The driving elements are elongate. They are flexible transverse to their longitudinal extent. They resist compression and tension forces along their longitudinal extent. Each pair of driving elements is secured at the other end of the instrument shaft to a respective instrument interface element of the instrument interface. Thus, the robot arm transfers drive to the end effector as follows: movement of a drive assembly interface element moves an instrument interface element which moves a driving element which moves one or more joints of the articulation and/or end effector which moves the end effector. The driving elements may be cables. The driving elements may comprise flexible portions and a rigid portion. Flexible portions engage the components of the instrument interface and the articulated coupling, and the rigid portion extends through all or part of the instrument shaft. For example, the flexible portion may be a cable, and the rigid portion may be a spoke. Other rigid portion(s) may be in the instrument interface or articulated coupling of the instrument. For example, rack and pinions may be in the instrument interface or articulated coupling of the instrument.

FIGS. 2a and 2b illustrate a first pair of driving elements A1, A2 which are constrained to move around the first yaw joint 207. Driving elements A1, A2 drive rotation of the first end effector element 209 about the first yaw axis 208. FIGS. 2a and 2b illustrate a second pair of driving elements B1, B2 which are constrained to move around the second yaw joint 211. Driving elements B1, B2 drive rotation of the second end effector element 210 about the second yaw axis 212. FIGS. 2a and 2b also illustrate a third pair of driving elements C1, C2 which are constrained to move around pitch joint 204. Driving elements C1, C2 drive rotation of the end effector 201 about the pitch axis 205. The end effector 201 can be rotated about the pitch axis 205 by applying tension to driving elements C1 and/or C2. The pitch joint 204 and yaw joints 207, 211 are independently driven by their respective driving elements.

The end effector elements 209 and 210 are independently rotatable. The end effector elements can be rotated in opposing rotational directions. For example, the end effector elements can be rotated in opposing rotational directions towards each other by applying tension to driving elements A2 and B1. This closes the end effector elements together, which is useful for (i) gripping an object between the end effector elements, such as tissue or a needle or thread, and/or (ii) cutting an object between the end effector elements, such as tissue or thread. The end effector elements can be rotated in opposing rotational directions away from each other by applying tension to driving elements A1 and B2. This opens the end effector elements, which is useful for (i) releasing an object which has been grasped between the end effector elements, and/or (ii) reopening a pair of scissor end effector elements ready for another cutting action. Both end effector elements can be rotated in the same rotational direction, by applying tension to driving elements A1 and B1 or alternatively A2 and B2. This causes the end effector elements to yaw about the pivot axes 208 and 212. This is useful for enabling the end effector to access a different part of the surgical site. Alternatively, one end effector element can be rotated (in either rotational direction) whilst the other end effector element is maintained in position, by applying tension to only one of driving elements A1, A2, B1, B2. Thus, both a gripping motion and a yawing motion of the end effector are enabled by manipulating the same pairs of driving elements: A1, A2 for the first end effector element 209, and B1, B2 for the second end effector element 210.

Any type of instrument having opposable end effector elements is relevant to the following description. A first exemplary type is cutting instruments, for which the end effector elements engage so as to cut tissue or another object between the end effector elements. A second exemplary type is gripping instruments, for which the end effector elements engage so as to grasp tissue or another object between the end effector elements.

The surgeon console comprises one or more surgeon input devices. Each surgeon input device enables the surgeon to provide a control input to the control system. A surgeon input device may, for example, be a hand controller, a foot controller such as a pedal, a touch sensitive input to be controlled by a finger or another part of the body, a voice control input device, an eye control input device or a gesture control input device. The surgeon input device may provide several inputs which the surgeon can individually operate.

Figure 3:
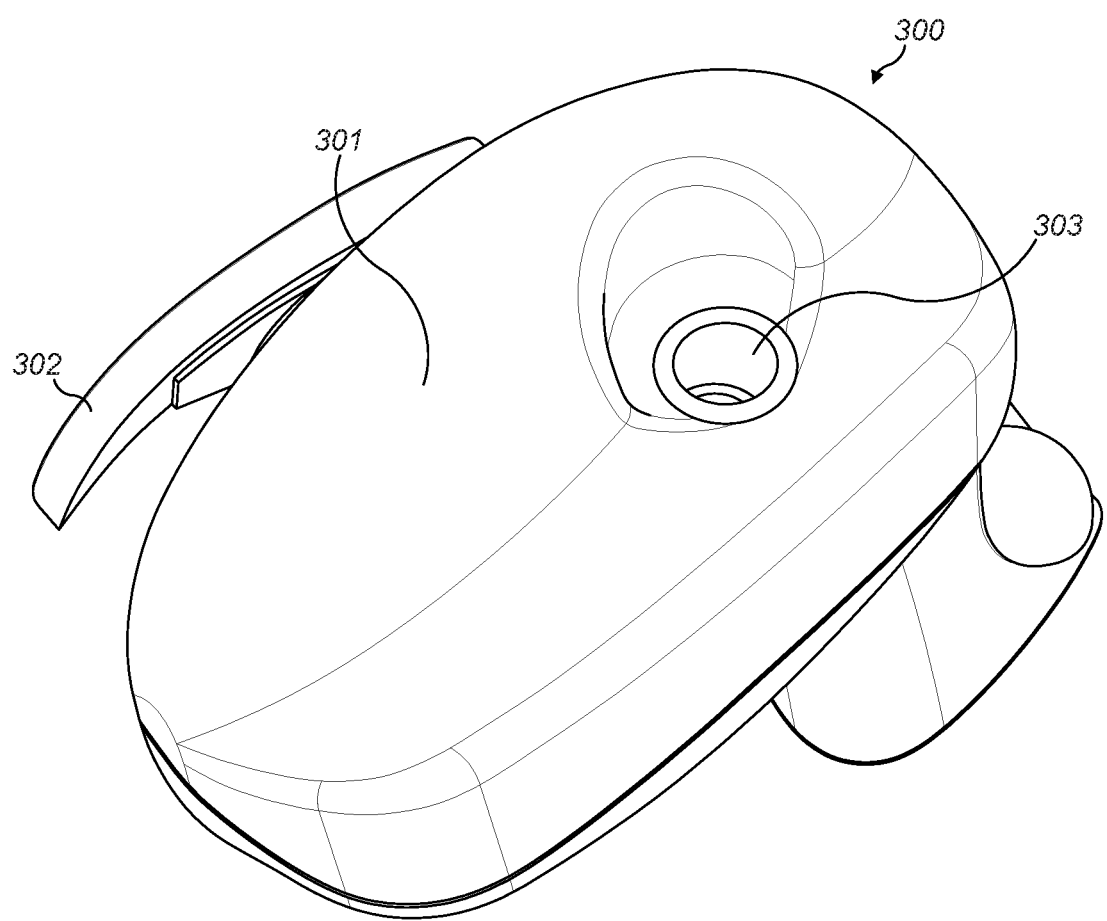
FIG. 3 illustrates an exemplary surgeon input device.

FIG. 3 illustrates an exemplary hand controller 300. The hand controller is connected to the surgeon console, for example by a gimbal arrangement (not shown). This enables the hand controller to be moved with three degrees of translational freedom with respect to the surgeon console. The hand controller shown is intended to be held by a right hand. A mirror image hand controller could be held by a left hand. The hand controller comprises a body 301 suitable for being gripped by a hand. The hand controller may comprise additional inputs, for example buttons, switches, levers, slide inputs or capacitive sensor inputs such as track pads 303. The hand controller of FIG. 3 comprises a trigger 302. The trigger 302 is movable relative to the body 301. In the hand controller shown, the trigger 302 is rotatable relative to the body 301. Alternatively, or in addition, the trigger could translate linearly relative to the body 301. The hand controller may comprise two triggers, each trigger for independently controlling a single different one of the end effector elements 209, 210.

The surgeon may rotate the trigger 302 relative to the body 301 of the hand controller in order to command the end effector elements 209, 210 of the instrument to close in a gripping/closing motion or to open in a releasing/opening motion. For example, the surgeon may rotate the trigger 302 towards the body 301 of the hand controller to command a gripping/closing motion. The surgeon may rotate the trigger 302 away from the body 301 of the hand controller to command a releasing/opening motion. The surgeon may rotate the body of the hand controller in the hand controller workspace to command a change in orientation of the end effector elements.

A control system connects the surgeon console to the surgical robot. The control system comprises a processor and a memory. The memory stores, in a non-transient way, software code that can be executed by the processor to cause the processor to control the surgeon console and robot arm and instrument in the manner described herein. The control system receives the inputs from the surgeon input device(s) and converts these to control signals to move the joints of the robot arm and/or the joint(s) of the articulated coupling and/or the joint(s) of the end effector. The control system sends these control signals to the robot arm, where the corresponding joints are driven accordingly. Manipulation of the surgical instrument is thereby controlled by the control system in response to manipulation of the surgeon input device.

When the control system is controlling an instrument having opposable end effector elements, on detecting an opening motion of the hand controller, the control system responds by commanding a force to be applied to the driving elements of the end effector elements to cause the end effector elements to rotate in opposing rotational directions away from each other. Referring to FIGS. 2a and 2b, the control system responds to detecting the opening motion by commanding a force to be applied to A1 and a force to be applied to B2, thereby causing the end effector elements to spread apart.

On detection of a second motion of the hand controller in the hand controller workspace, the control system may respond by commanding articulation of any one or combination of: (i) the joints of the surgical robot arm, (ii) the joints of the articulated coupling 203 of the surgical instrument, and (iii) the joints of the end effector. This commanded articulation causes the pose of the end effector to change as directed by the second motion. For example, the second motion may be a rotation of the body 301 of the hand controller. As another example, the second motion may be manipulation of a further input on the hand controller, for example movement of a further trigger. That movement may be a rotation of the further trigger relative to the body of the hand controller. Alternatively, or in addition, the further trigger could translate linearly relative to the body 301.

Thus, the control system may respond to detection of the second motion (such as rotation) of the body of the hand controller by, at least in part, commanding forces to be applied to the driving elements of the end effector elements to cause the end effector elements to rotate. For example, referring to FIGS. 2a and 2b, the control system may command forces to be applied to A2 and B2 to cause the end effector elements 209 and 210 to yaw in a clockwise direction. The control system may command forces to be applied to A1 and B1 to cause the end effector elements 209 and 210 to yaw in an anti-clockwise direction. The control system may command the same force to be applied to both A1 and B1 (or A2 and B2). If the end effector elements match, and the driving elements for those end effector elements match, then for a configuration in which the end effector elements are not fully closed and exerting a forces against each other, applying the same force to both A1 and B1 (or A2 and B2) causes both end effectors elements to yaw in unison. The control system may also respond to detection of the second motion (such as rotation) of the body of the hand controller by commanding forces to be applied to one of C1 and C2 to cause a rotation of the pitch joint 204. The control system may also respond to detection of the second motion (such as rotation) of the body of the hand controller by commanding torques to be applied about one or more of the joints of the robot arm.

The same driving elements A1, A2 and B1, B2 are utilised to drive rotation of the end effector elements for both opening and closing the end effector elements relative to each other and yawing the end effector. Thus, the opening/closing and yawing operations are not independently driven.

Figure 4:
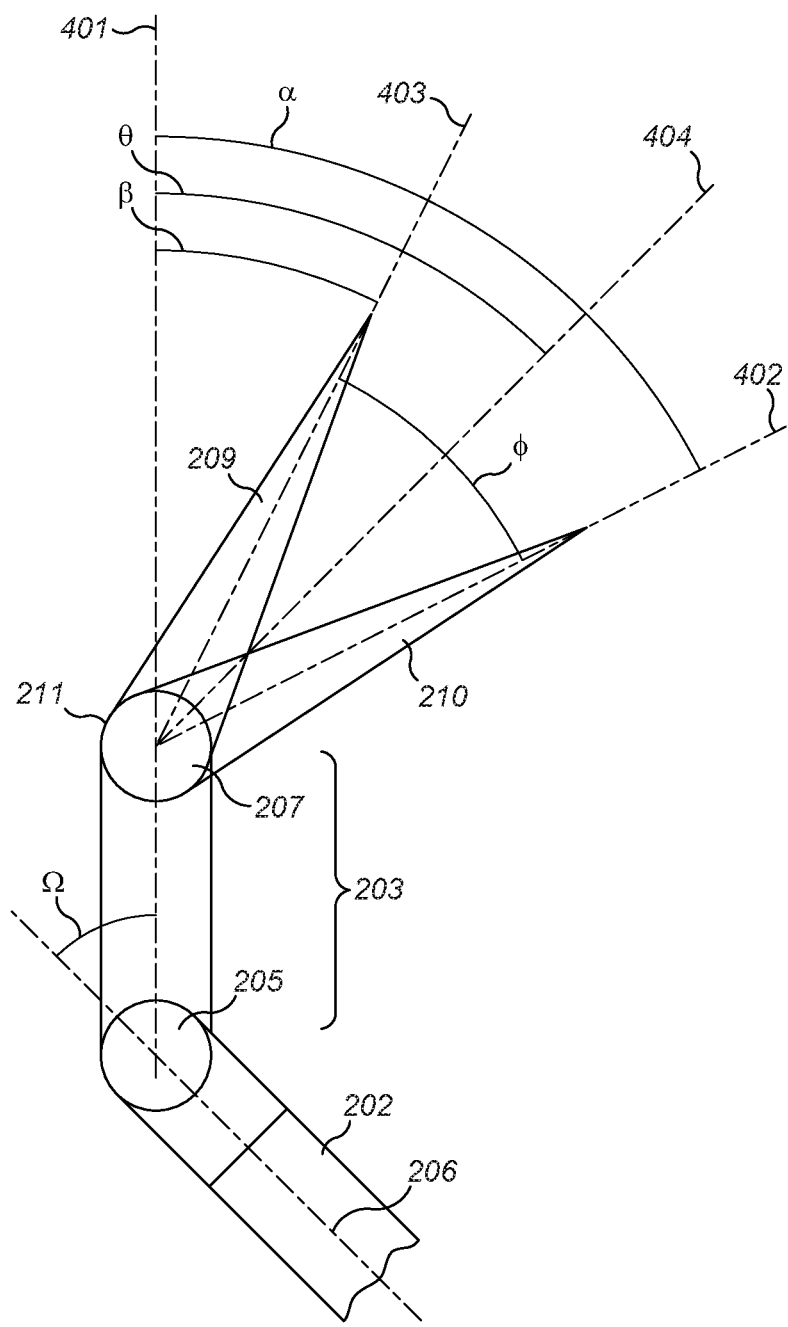
FIG. 4 illustrates the distal end of an exemplary surgical instrument.

Referring to FIG. 4, each end effector element 209, 210 is capable of rotating about the axis of its connected joint 207, 211 with respect to the longitudinal axis 401 of the articulated coupling 203. The longitudinal axis 402 of the end effector element furthest from the longitudinal axis 401 of the articulated coupling 203 is depicted in FIG. 4 as being separated from the longitudinal axis 401 of the articulated coupling 203 by an angle $\alpha$. The longitudinal axis 403 of the end effector element closest to the longitudinal axis 401 of the articulated coupling 203 is depicted in FIG. 4 as being separated from the longitudinal axis 401 of the articulated coupling 203 by an angle $\beta$. The end effector elements are separated by a spread of $\phi$. In other words, the angle between the longitudinal axes 402 and 403 of the end effector elements is $\phi$.

Each end effector element is limited in how far it can rotate about the axis of its connected joint. The maximum rotational angle between the longitudinal axis 402 of the furthest end effector and the longitudinal axis 401 of the articulated coupling 203 is $\alpha_{max}$. For example, $\alpha_{max}$ may be in the range 60° to 90°. $\alpha_{max}$ may be in the range 65° to 80°. $\alpha_{max}$ may be 70°. $\alpha_{max}$ may be instrument dependent. The end effector elements may be opened to a spread angle $\phi$, and then yawed clockwise as shown in FIG. 4. As the end effector elements yaw, the opening angle $\phi$ is initially maintained. However, once the furthest end effector element 210 reaches its rotation limit at an angle of $\alpha_{max}$ it stops rotating. If the surgeon input device continues to command a yawing action, and the control system continues to drive the instrument accordingly, then the end effector element 210 remains still, but the other end effector element 209 continues to yaw, i.e. continues to rotate clockwise. Thus, the opening angle $\phi$ starts to decrease, and hence the end effector elements start to close, even though the surgeon input device is still commanding the end effector elements to remain open.

In FIG. 4, the end effector is illustrated as having yawed in a clockwise direction relative to the longitudinal axis 401 of the articulated coupling. End effector element 210 is thus furthest from the longitudinal axis 401 of the articulated coupling. The maximum rotation angle between the axes 402 and 401 is $\alpha_{max}$. When the end effector yaws in an anticlockwise direction relative to the longitudinal axis 401 of the articulated coupling, then the end effector element 209 is furthest from the longitudinal axis 401 of the articulated coupling. In this scenario, the maximum rotational angle between the axes 401 and 403 is $\alpha_{max}$. The maximum rotation angle $\alpha_{max}$ may be the same for both a clockwise rotation of one end effector element and an anticlockwise rotation of the other end effector element. This may be the case for symmetrical instruments. For other instruments, the maximum rotation angle $\alpha_{max}$ may be different for a clockwise rotation of one end effector element and an anticlockwise rotation of the other end effector element. For example, this may be the case for asymmetrical instruments. For some asymmetrical instruments, the end effector elements may have a range of motion which is restricted to one side only of the longitudinal axis 401 of the articulated coupling. In this scenario, the same end effector element is always furthest from the longitudinal axis 401 of the articulated coupling.

The end effector elements may also be limited in how far they can rotate away from each other. For example, the opening angle may be limited to $\phi_{max}$. $\phi_{max}$ may be instrument dependent. For example, $\phi_{max}$ may be in the range 40° to 90°. $\phi_{max}$ may be in the range 45° to 75°.

Figure 5:
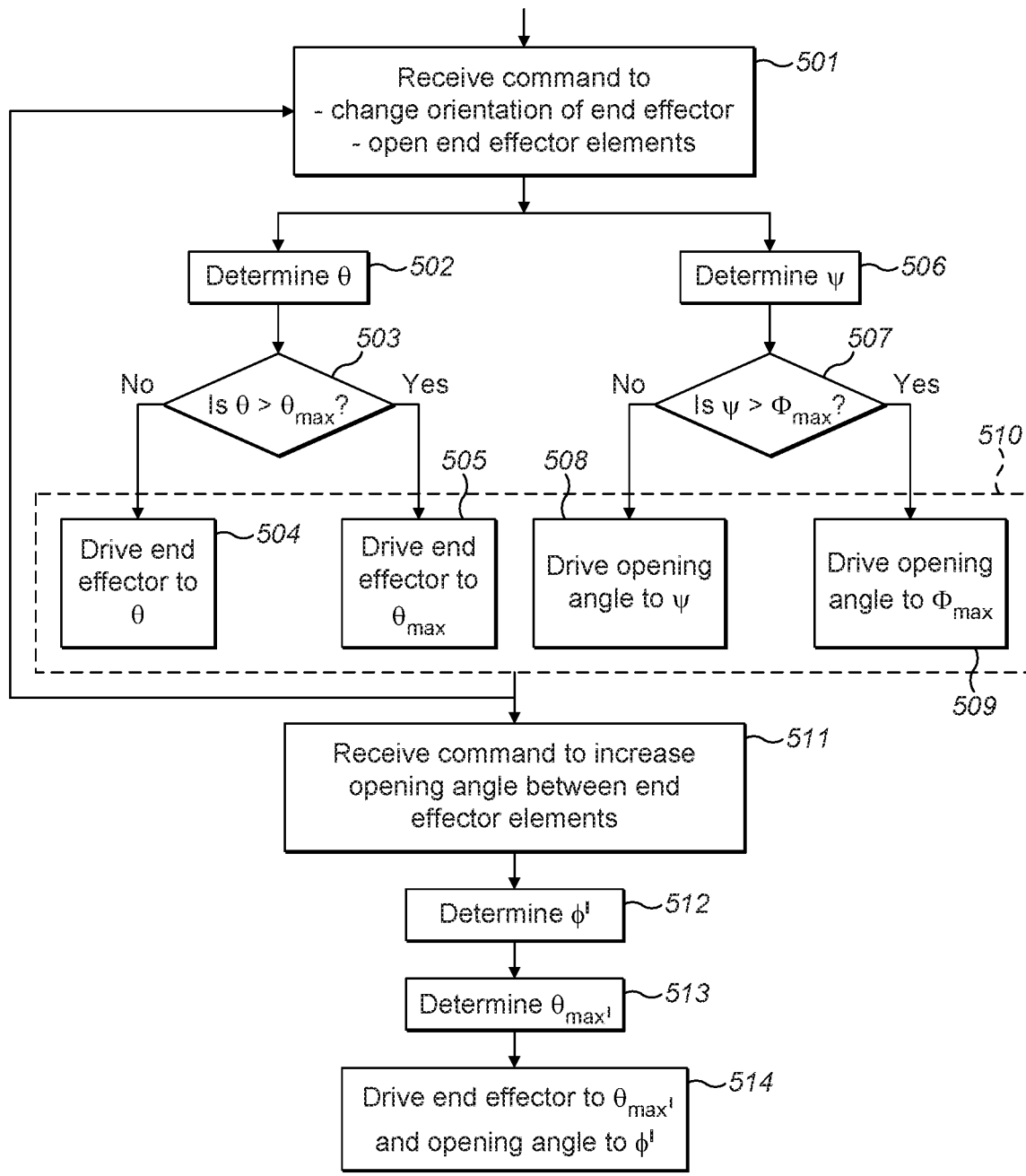
FIG. 5 is a flowchart of a method of controlling manipulation of a surgical instrument.

FIG. 5 illustrates a method implemented by the control system to limit the yawing motion of the end effector so as to prioritise maintenance of the opening angle of the end effector elements.

At step 501 of FIG. 5, the control system receives a command from the surgeon input device to both (i) change the orientation of the end effector, and (ii) open the end effector elements relative to each other.

As described above, the command from the surgeon input device to change the orientation of the end effector may be a rotation of the surgeon input device in its workspace. The surgeon input device may be connected to the surgeon console by an articulated linkage, optionally including a gimbal assembly. A position sensor may be included on each movable joint of the articulated linkage. The control system receives the sensed positions of each joint of the articulated linkage. From the known order, masses and lengths of the links and joints in the articulated linkage, and the received sensed positions, the control system determines the change of orientation of the surgeon input device. From the change of orientation of the surgeon input device, the control system determines the commanded change of orientation of the end effector.

The command from the surgeon input device to open the end effector elements relative to each other may be a rotation of the trigger away from the body of the surgeon input device. Alternatively, a command from the surgeon input device to open the end effector elements relative to each other may be a linear translation of the trigger relative to the body. For example, the hand controller 300 of FIG. 3 may include a position sensor which senses the rotational (or linear) position of the trigger 302 relative to the body 301 of the hand controller. The control system receives the sensed rotational (or linear) position of the trigger from the position sensor.

At step 502, in response to the command to change the orientation of the end effector, the control system determines an angle $\theta$ between the longitudinal axis of the articulated coupling and the end effector. FIG. 4 illustrates $\theta$ as between the longitudinal axis 401 of the articulated coupling and an axis 404 which bisects the end effector elements. In FIG. 4, the bisecting axis 404 is such that (i) axes 402, 403 and 404 all intersect at a point, and (ii) the angle between the axes 402 and 404 is equal to the angle between the axes 403 and 404. The axes 402, 403 and 404 intersect where they meet the yaw axes 207 and 212.

The angle $\theta$ is that determined to effect the change in orientation commanded by the surgeon input device. The angle $\theta$ may be proportional to the angle through which the surgeon input device has rotated in its workspace. In the case that a change in orientation is commanded by motion of part of the surgeon input device, such as a further trigger, then the angle $\theta$ may be proportional to the angle through which that part of the surgeon input device has rotated, or the distance along which that part of the surgeon input device has linearly translated.

At step 503, the control system compares $\theta$ to $\theta_{max}$. $\theta_{max}$ is the maximum value of $\theta$. In other words, $\theta_{max}$ is the maximum angle between the longitudinal axis 401 of the articulated coupling and the end effector. $\theta_{max}$ may be a function of the opening angle of the end effector elements $\phi$. Alternatively, or additionally, $\theta_{max}$ may be a function of the maximum rotational angle $\alpha_{max}$ of the furthest end effector element. For example, $$\alpha_{max} = \alpha_{max} - \phi/2 \qquad \text{(equation 1)}$$

The control system determines whether $\theta > \theta_{max}$. If $\theta \leq \theta_{max}$, then controlling the end effector elements to rotate such that the angle between the longitudinal axis 401 of the articulated coupling and the end effector is $\theta$ will not cause the opening angle of the end effector elements to start closing. Thus, if $\theta \leq \theta_{max}$, then at step 504, the control system drives the first and second end effector elements to rotate such that the angle between the longitudinal axis 401 of the articulated coupling and the end effector is $\theta$. For example, the angle between the longitudinal axis 401 of the articulated coupling and the bisecting axis 404 is $\theta$.

If, at step 503, the control system determines that $\theta > \theta_{max}$, then controlling the end effector elements to rotate such that the angle between the longitudinal axis 401 of the articulated coupling and the end effector is $\theta$ will cause the opening angle of the end effector elements to start closing. Thus, instead, at step 505, the control system drives the first and second end effector elements to rotate such that the angle between the longitudinal axis 401 of the articulated coupling and the end effector is $\theta_{max}$. For example, the angle between the longitudinal axis 401 of the articulated coupling and the bisecting axis 404 is $\theta_{max}$.

Meanwhile, the control system determines to drive an opening angle $\phi$ between the first and second end effector elements. At step 506, in response to the command to open the end effector elements, the control system determines an opening angle $\psi$ between the first and second end effector elements. Specifically, $\psi$ is the angle between the longitudinal axis of the first end effector element 402 and the longitudinal axis of the second end effector element 403. The angle $\psi$ is that determined to effect the opening angle between the end effector elements commanded by the surgeon input device. The angle $\psi$ may be proportional to the rotational position of the trigger relative to the body of the surgeon input device once the trigger has been moved to effect the command of step 501.

At step 507, the control system compares $\psi$ to $\phi_{max}$. The control system determines whether $\psi > \phi_{max}$. If $\psi \leq \phi_{max}$, then at step 508, the control system drives the first and second end effector elements to rotate such that the angle between the longitudinal axes 402 and 403 of the end effector elements $\phi = \psi$.

If at step 507, the control system determines that $\psi > \phi_{max}$, then at step 509, the control system drives the first and second end effector elements to rotate such that the angle between the longitudinal axes 402 and 403 of the end effector elements $\phi = \phi_{max}$.

On FIG. 5, steps 504, 505, 508 and 509 are all encased within a dashed step 510. This is to indicate that those ones of steps 504, 505, 508 and 509 which are implemented in a given iteration of the control method of FIG. 5 are done so in concert. For example, If the answer to both steps 503 and 507 is NO, then steps 504 and 508 are performed in concert. If the answer to both steps 503 and 507 is YES, then steps 505 and 509 are performed in concert. If the answer to step 503 is NO and the answer to step 507 YES, then steps 504 and 509 are performed in concert. If the answer to step 503 is YES and the answer to step 507 NO, then steps 505 and 508 are performed in concert.

Performed in concert means that the control system determines the forces to be applied to the first pair of driving elements A1, A2 and the forces to be applied to the second pair of driving elements B1, B2 so as to cause both (i) the end effector to be driven to $\theta$ or $\theta_{max}$, and (ii) the opening angle to be driven to $\phi$ (i.e. $\psi$ or $\phi_{max}$).

In response to the command to change the orientation of the end effector, the control system may also determine an angle $\Omega$ between the longitudinal axis 206 of the shaft 202 and the longitudinal axis 401 of the articulated coupling 203. The angles $\theta$ and $\Omega$ are determined to together effect the change in orientation commanded by the surgeon input device. For example, the combined angle $\theta + \Omega$ may be proportional to the angle through which the surgeon input device has been rotated in its workspace. In this scenario, at step 510, the control system drives the third pair of driving elements C1, C2 so as to cause the supporting body 213 and hence the end effector 201 to rotate about the pitch axis 205 by the angle $\Omega$.

After the end effector elements and/or supporting body have been driven to the angles described with reference to step 510, the control loop may repeat. In other words, a further command may be received by the control system to change the orientation of the end effector and open the end effector elements at step 501. In this case, the method described above repeats. Alternatively, a further command may be received by the control system to increase the opening angle between the end effector elements at step 511. For example, the trigger of the surgeon input device may have been rotated further away from the body of the surgeon input device. No command is received from the surgeon input device to change the orientation of the end effector. If at step 510, the end effector had been driven to $\theta_{max}$, then the furthest end effector element 210 is already at the maximum rotation angle $\alpha_{max}$ that it can sustain at the current opening angle of $\phi$.

In response to the further command at step 511, at step 512 the control system determines $\phi'$. $\phi'$ is an opening angle between the first and second end effector elements. $\phi'$ is determined to effect the opening angle between the end effector elements commanded by the surgeon input device at step 511. The angle $\phi'$ may be proportional to the rotational position of the trigger relative to the body of the surgeon input device once the trigger has been moved to effect the command of step 511.

Then, at step 513, the control system determines $\theta_{max}'$. $\theta_{max}'$ is the maximum angle between the longitudinal axis of the articulated coupling and the end effector which enables the opening angle $\phi'$ to be sustained. $\theta_{max}'$ may be a function of the opening angle of the end effector elements $\phi'$. Alternatively, or additionally, $\theta_{max}'$ may be a function of the maximum rotational angle $\alpha_{max}$ of the furthest end effector element. For example, $$\theta_{max}' = \alpha_{max} - \phi'/2 \quad \text{(equation 2)}$$

Then, at step 514, the control system drives the end effector elements to rotate such that (i) the angle between the longitudinal axis of the articulated coupling and the end effector is $\theta_{max}'$, and (ii) the opening angle between the first and second end effector elements is $\phi'$. Thus, in practice, the furthest end effector element 210 maintains its rotational position at $\alpha_{max}$, and the closest end effector element 209 is driven to rotate towards the longitudinal axis of the articulated coupling 401, thereby achieving the desired opening angle $\phi'$.

As a numerical example, consider a case where $\alpha_{max}=70°$. At step 508, the opening angle of the end effector elements is driven to $\phi=50°$. Thus, using equation 1, $\theta_{max}=45°$. At step 510, the end effector is driven to $\theta_{max}=45°$. Thus, the individual end effector elements are at 20° and 70° to the longitudinal axis 401 of the articulated coupling. At step 511, the control system receives a command from the surgeon input device to open the end effector elements to an opening angle of $\phi'=60°$. Since $\alpha_{max}=70°$, using equation 2, $\theta_{max}'=40°$. Thus, the individual end effector elements are at 10° and 70° to the longitudinal axis 401 of the articulated coupling.

Thus, the control method of FIG. 5 prevents the opening angle $\phi$ of the end effector elements from decreasing as the surgeon input device commands an increased yawing motion of the end effector. Maintaining the opening angle $\phi$ of the end effector elements is prioritised over maximising the angle from the longitudinal axis 401 of the articulated coupling to which each individual end effector element can rotate.

The steps illustrated in the control method of FIG. 5 are those relevant to the problem addressed herein. The control system performs many other steps during the control method of FIG. 5. Those other steps are not shown in FIG. 5.

The end effector may take any suitable form. For example, the end effector could be a pair of curved scissors, an electrosurgical instrument such as a pair of monopolar scissors, a needle holder, a pair of jaws, or a fenestrated grasper.

The robot described herein could be for purposes other than surgery. For example, the port could be an inspection port in a manufactured article such as a car engine and the robot could control a viewing tool for viewing inside the engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A control system configured to control manipulation of a surgical instrument in response to manipulation of a remote surgeon input device, the surgical instrument comprising an end effector having opposable first and second end effector elements connected to a shaft by an articulated coupling, the control system configured to:
   receive a command from the surgeon input device to both (i) change the orientation of the end effector, and (ii) open the first and second end effector elements relative to each other;
   in response to the command to change the orientation of the end effector, determine an angle $\theta$ between the longitudinal axis of the articulated coupling and the end effector;
   in response to the command to open the first and second end effector elements, determine an opening angle tri between the first and second end effector elements;
   compare $\theta$ to a maximum angle $\theta_{max}$ between the longitudinal axis of the articulated coupling and the end effector, wherein $\theta_{max}$ is a function of $\varphi$ and $\alpha_{max}$, $\alpha_{max}$ being the maximum rotation angle between the longitudinal axis of the articulated coupling and the end effector element furthest from the longitudinal axis of the articulated coupling; and
   if $\theta > \theta_{max}$, drive the first and second end effector elements to rotate such that (i) the angle between the longitudinal axis of the articulated coupling and the end effector is $\theta_{max}$, and (ii) the opening angle between the first and second end effector elements is $\varphi$.

2. The control system as claimed in claim 1, configured to, if $\theta \leq \theta_{max}$, drive the first and second end effector elements to rotate such that (i) the angle between the longitudinal axis of the articulated coupling and the end effector is $\theta$, and (ii) the opening angle between the first and second end effector elements is $\varphi$.

3. The control system as claimed in claim 1, wherein the angle $\theta$ is between the longitudinal axis of the articulated coupling and an axis which bisects the end effector elements.

4. The control system as claimed in claim 1, wherein $\theta_{max} = \alpha max - \varphi/2$.

5. The control system as claimed in claim 1, wherein the command from the surgeon input device to change the orientation of the end effector comprises a rotation of at least a portion of the surgeon input device in its workspace.

6. The control system as claimed in claim 1, wherein the opposable first and second end effector elements are one of: a pair of jaws, a pair of scissors, and a needle driver.

7. The control system as claimed in claim 1, wherein the surgeon input device comprises a body and a trigger, and wherein the command from the surgeon input device to open the first and second end effector elements relative to each other comprises a movement of the trigger relative to the body.

8. The control system as claimed in claim 7, configured to determine the opening angle $\varphi$ between the first and second end effector elements by:

in response to the command to open the first and second end effector elements, determine an opening angle $\psi$ to effect the opening angle between the end effector elements commanded by the surgeon input device, wherein $\psi$ is proportional to the rotational position of the trigger relative to the body of the surgeon input device;

compare $\psi$ to a maximum angle $\varphi_{max}$ between the first and second end effector elements; and if $\psi > \varphi_{max}$, drive the first and second end effector elements to rotate such that the opening angle between the first and second end effector elements $\varphi = \varphi_{max}$.

9. The control system as claimed in claim 8, configured to, if $\psi \leq \varphi_{max}$, drive the first and second end effector elements to rotate such that the opening angle between the first and second end effector elements $\varphi = \psi$.

10. The control system as claimed in claim 7, wherein the command from the surgeon input device to open the first and second end effector elements relative to each other comprises a rotation of the trigger away from the body.

11. The control system as claimed in claim 10, wherein the angle between the trigger and the body at the end of the rotation is proportional to $\varphi$.

12. The control system as claimed in claim 7, wherein the command from the surgeon input device to open the first and second end effector elements relative to each other comprises a linear translation of the trigger relative to the body.

13. The control system as claimed in claim 1, wherein the articulated coupling comprises a first joint driveable by a first pair of driving elements, and a second joint driveable by a second pair of driving elements, and wherein the control system is configured to drive the first and second end effector elements to rotate by:

commanding a first force to be applied to the first pair of driving elements so as to cause the first end effector element to rotate about the first joint; and commanding a second force to be applied to the second pair of driving elements so as to cause the second end effector element to rotate about the second joint.

14. The control system as claimed in claim 1, configured to:

following driving the first and second end effector elements to rotate such that the angle between the longitudinal axis of the articulated coupling and the end effector is $\theta_{max}$, receive a further command from the surgeon input device to increase the opening angle between the first and second end effector elements relative to each other;

in response to the further command:

determine an opening angle $\varphi'$ if between the first and second end effector elements;

determine an angle $\theta_{max}'$ between the longitudinal axis of the articulated coupling and the end effector, where $\theta_{max}'$ is a function of if $\varphi'$; and drive the first and second end effector elements to rotate such that (i) the angle between the longitudinal axis of the articulated coupling and the end effector is $\theta_{max}'$, and (ii) the opening angle between the first and second end effector elements is $\varphi$.

15. The control system as claimed in claim 14, wherein $\theta_{max}' = \alpha_{max} - '/2$, where $\alpha_{max}$ is the maximum rotation from the longitudinal axis of the articulated coupling of the end effector element in the commanded direction of rotation.

16. The control system as claimed in claim 13, wherein each of the first and second pairs of driving elements comprises cables.

17. The control system as claimed in claim 13, wherein the first force, second force and/or third force are tension forces.

18. The control system as claimed in claim 13, wherein the articulated coupling further comprises a third joint driveable by a third pair of driving elements, and wherein the control system is configured to:

in response to the command to change the orientation of the end effector, determine an angle $\Omega$ between the longitudinal axis of the shaft and the longitudinal axis of the articulated coupling; and drive the end effector to rotate about the third joint by $\Omega$.

19. The control system as claimed in claim 18, wherein the control system is configured to drive the end effector to rotate about the third joint by commanding a third force to be applied to the third pair of driving elements so as to cause the end effector to rotate about the third joint.

* * * * *